(12) United States Patent
Nielsen

(10) Patent No.: US 10,363,417 B2
(45) Date of Patent: Jul. 30, 2019

(54) IMPLANT FIXATION AND IMPACT DISPLACEMENT PROTECTION SYSTEMS

(71) Applicant: MED-EL Elektromedizinische Geraete GmbH, Innsbruck (AT)

(72) Inventor: Stefan B. Nielsen, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 260 days.

(21) Appl. No.: 14/768,779

(22) PCT Filed: Mar. 5, 2014

(86) PCT No.: PCT/US2014/020496
§ 371 (c)(1),
(2) Date: Aug. 19, 2015

(87) PCT Pub. No.: WO2014/138149
PCT Pub. Date: Sep. 12, 2014

(65) Prior Publication Data
US 2016/0001076 A1  Jan. 7, 2016

Related U.S. Application Data

(60) Provisional application No. 61/773,866, filed on Mar. 7, 2013.

(51) Int. Cl.
*A61N 1/36* (2006.01)
*A61N 1/05* (2006.01)
(Continued)

(52) U.S. Cl.
CPC ....... *A61N 1/36032* (2013.01); *A61N 1/0541* (2013.01); *A61N 1/36036* (2017.08);
(Continued)

(58) Field of Classification Search
CPC ... A61N 1/36032; A61N 1/375; H04R 25/606
See application file for complete search history.

(56) References Cited

U.S. PATENT DOCUMENTS 7,346,391 B1 * 3/2008 Osorio ................. A61B 5/0476
600/378
7,937,156 B2 * 5/2011 Gibson ................. A61N 1/0541
607/115

(Continued)

FOREIGN PATENT DOCUMENTS

WO  WO 2007053882 A1  5/2007

OTHER PUBLICATIONS

International Searching Authority, Authorized Officer J. Smit, International Search Report and Written Opinion, PCT/US2009/054580, dated Dec. 10, 2009, 9 pages.

(Continued)

*Primary Examiner* — George R Evanisko
(74) *Attorney, Agent, or Firm* — Sunstein Kann Murphy & Timbers LLP

(57) ABSTRACT

A cochlear implant system is described which includes an implant housing containing a stimulation processor for processing externally produced communications signals to generate electrical stimulation signals for the cochlea of an implant patient. The implant housing lies substantially in a plane and has an outer perimeter adapted to fit within a surgically prepared housing recess in skull bone of the implant patient. Multiple housing fixation features are located on the outer perimeter and cooperate to develop lateral force in the plane of the implant housing between the implant housing and adjacent skull bone of the housing recess to fixedly secure the implant housing within the housing recess.

17 Claims, 14 Drawing Sheets

(51) Int. Cl.
  *A61N 1/372* (2006.01)
  *A61N 1/375* (2006.01)
  *H04R 25/00* (2006.01)

(52) U.S. Cl.
  CPC ......... *A61N 1/375* (2013.01); *A61N 1/37223* (2013.01); *H04R 25/606* (2013.01)

(56) References Cited

U.S. PATENT DOCUMENTS

| | | |
|---|---|---|
| 8,255,058 B2 | 8/2012 | Gibson et al. |
| 2004/0088024 A1 | 5/2004 | Firlik et al. |
| 2004/0260361 A1 | 12/2004 | Gibson |
| 2006/0116743 A1 | 6/2006 | Gibson et al. |
| 2007/0123923 A1 | 5/2007 | Lindstrom et al. |
| 2008/0195178 A1 | 8/2008 | Kuzma |
| 2009/0209806 A1* | 8/2009 | Hakansson .......... H04R 25/606 600/25 |
| 2010/0049318 A1 | 2/2010 | Jolly et al. |
| 2011/0245891 A1* | 10/2011 | Fritsch ................. A61N 1/0541 607/57 |
| 2013/0018218 A1* | 1/2013 | Haller .................... H04R 25/60 600/25 |

OTHER PUBLICATIONS

International Searching Authority, Authorized Officer Shane Thomas, International Search Report and Written Opinion, PCT/US14/20496, dated Jun. 6, 2014, 15 pages.

* cited by examiner

IMPLANT FIXATION AND IMPACT DISPLACEMENT PROTECTION SYSTEMS

This application is a National Phase Entry application of co-pending Patent Cooperation Treaty Patent Application PCT/US2014/020496, filed Mar. 5, 2014, which in turn claims priority from U.S. Provisional Patent 61/773,866, filed Mar. 7, 2013, both of which are incorporated herein by reference.

TECHNICAL FIELD

The present invention relates to hearing implant systems such as cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant (CI) that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission via external coil 107 into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through wires in an electrode lead 109 to an implanted electrode array 110. Typically, the electrode array 110 includes multiple electrodes on its surface that provide selective stimulation of the cochlea 104.

Conventionally, the implant housing is placed in a bony bed or flattened area drilled on the skull bone. This is done for various reasons including improved stability and protection when external forces act on the implant housing. Recessing the implant housing in the skull bone also reduces the amount by which the implant housing protrudes out from the bone surface towards the skin and makes the implant bump on the skin less obvious when seen from the outside.

Adults have comparatively thick skull bones which generally allow the drilling of deep implant beds and consequently a good fixation of the device. But the skull bones in children are much thinner and it may be difficult to sufficiently recess the implant housing without drilling all the way through the skull bone down to the outer layer of the cerebral membrane, the dura mater. In many young patients, the implanting surgeon decides to remove all underlying bone in order to obtain an appropriately recessed implant housing.

Removing the bone volume in the implant bed by layer by layer drilling is a time consuming task, and minimizing the implant surgery time is gradually becoming more important, not only to minimizes the costs of surgery, but also to reduce the time that the implant patient is under general anesthetic. Therefore, some surgeons use a faster method of making the housing recess where they only drill down to the dura mater along the contour of the implant and pry out the remaining central bone island. This leaves a well that goes all the way through the skull bone, i.e. a recess of maximum possible depth.

Other tasks that can take considerable amounts of time during implantation surgery include fixation of the implant housing in the bony recess. While specific implant fixation (e.g. tying down with sutures) is strongly recommended by cochlear implant manufacturers, some surgeons prioritize a shorter surgery time over the benefits of direct implant fixation and do not specifically fixate the device. Commonly practiced indirect fixations are achieved by tightly closing the periosteum over the implant housing and suturing the surgical opening in the skin over the implantation site.

Even though such methods provide some fixation of the implant housing, they are likely to leave the device in just a semi-fixated situation, at least initially and depending on how well the housing recess was drilled to fit the implant housing. If a deep enough housing recess has been made, the implant housing may be appropriately immobilized in the lateral direction by the bone surrounding the implant housing. But in the perpendicular up-down directions (away from/toward the center of the head), the fixation will most likely be inadequate, especially if there is no bone underneath the implant housing. Movements in towards the brain may occur, for example, when the patient presses on the implant by hand or rests their head on the implant location. Movements in both directions (up/down) may originate from blood pressure pulsations in the brain that make the cerebral membranes move—since the implant housing rests on these membranes it will likely experience similar types of movements.

In an upward direction away from the center of the head, movement of the implant housing is only limited by the periosteum and the skin if there is no direct implant fixation. The periosteum is a dense connective tissue, so it has a limited ability to elongate when non-permanent forces act on it, but it will remodel over time to relieve any permanent tension that may be present, thus becoming a largely tension-free but tightly fitting cover over the implant housing after some period of time.

In its natural condition the periosteum adheres quite strongly to the skull bone. During the surgical implantation procedure this tissue is intentionally loosened from the underlying skull bone to expose an area where the housing recess can be made and to create a periosteal pocket for the implant coil. Normally the periosteum is loosened over an area significantly larger than the implant housing leaving a fairly lose cover over the device directly after implantation, but over time the loosened periosteum will re-attach to the bone by scar tissue formation.

Young cochlear implant users are likely to be reimplanted several times during their lives, thus necessitating repeated surgery at the same location. Thus it is should be assumed that a gradual destruction of the periosteum and its fixating function in the upward direction occurs. Over time new bone tissue will be generated around the implant housing so that it eventually will be found in a well-fitting implant bed. Implant fixation methods also should allow the device to be easily removed if it, for example, becomes non-functional and needs replacement or if the user desires a technological upgrade to a newer device.

Downward (inward) directed movements of the implant housing are generally resisted only by the bone beneath the device and by any parts of the implant system that are attached to the implant housing (e.g. the coil and electrodes) which lie on top of the bone. In cases where all of the bone down to the dura mater has been removed during implantation, some immobilizing function may be provided by the outer cerebral membrane directly underneath the housing which normally adheres to the inside of the skull bone. In many cases, new bone regrows over time over the cerebral membrane giving a better fixation below the implant housing than from just the membrane alone.

Modern CI's are designed to withstand an increased level of impact energy before they become non-functional to be robust against accidental impacts. However, this may be of secondary importance if the impact energy cannot be directed onto stable structures that can take such impact loads without being damaged. If there is no or little bone beneath the implant housing, then there is an inherent risk of the implant housing being displaced in towards the brain when external forces strike the implant (e.g. from a CI user accidentally falling and hitting the head). This risk goes together with increased risks of hemorrhages and other tissue damages in the area of the brain which can have serious consequences.

In recent years some efforts have been made to develop ways of easy, fast, reliable, and safe fixation of implantable neuro-stimulators such as cochlear implants. Direct and indirect suturing of the implant housing are the most common ways of securing the devices, but more and more surgeons are moving away from direct suturing, either due to time (and cost) concerns or because they believe that this type of fixation is not needed. However, many surgeons do not realize that inappropriate fixation can have a detrimental effect on the long term functionality of the device and so initially saving surgery time could well result in early device failure and the need for an early device replacement surgery.

U.S. Patent Publication 2010-0049318 describes some ways to fix the implant housing to the bone underneath the device. But if there is no or little bone under the implant housing, then some of the described fixation methods are inappropriate. Similar concepts are described in U.S. Patent Publication 2006-0116743 where one or more flanges extend outward from the implant housing for fixation to the tissue. U.S. Patent Publication 2009-0209806 describes a bone conductor transducer that is connected to the skull bone to transmit vibrations using static force methods.

SUMMARY

Embodiments of the present invention are directed to a cochlear implant system which includes an implant housing containing a stimulation processor for processing externally produced communications signals to generate electrical stimulation signals for the cochlea of an implant patient. The implant housing lies substantially in a plane and has an outer perimeter adapted to fit within a surgically prepared housing recess in skull bone of the implant patient. Multiple housing fixation features are located on the outer perimeter and cooperate to develop lateral force in the plane of the implant housing between the implant housing and adjacent skull bone of the housing recess to fixedly secure the implant housing within the housing recess.

The housing fixation features may include one or more fixed contact features located toward one side of the outer perimeter and one or more elastic spring features located towards another side of the outer perimeter. The spring features may be embedded in resiliently compressible material. The spring features may be adapted to be bendable in a plane perpendicular to the housing plane. The spring features may include an elongated contact strip along a portion of the outer perimeter. The spring features may include a pair of elastic spring pins. For example, the spring pins may be compressible in towards each other along an axis tangent to the outer perimeter or along a chord across the outer perimeter. And the spring pins may include one or more rotation resisting features adapted to resist rotation of the implant housing within the housing recess. The spring features may be formed of metal spring material such as titanium and/or elastic polymer material. For example, the spring features and the housing may be formed from a single common piece of titanium material.

The fixed contact features include an elongated contact strip along a portion of the outer perimeter and/or multiple fixed contact pins. The fixed contact features may be shaped to allow an opposite side of the outer perimeter to be lifted up out of the housing recess without damaging the skull bone around the fixed pins.

The housing fixation features may include active features adapted to be manually operated during insertion surgery to fixedly secure the implant housing within the housing recess. For example, the active features may be based on a screw mechanism.

Embodiments may further include a receiver coil adjacent to the implant housing for receiving the communications signals from an external transmitter coil on the skin of the patient over the receiver coil. Some embodiments may further include multiple implant protection features located on the outer perimeter and protruding above the outer surface of the skull bone around the housing recess to resist inward displacement of the implant housing in response to an external impact force normal to the implant housing.

DETAILED DESCRIPTION

Embodiments of the present invention are directed to fixating the implant housing in an easy, fast, reliable and safe manner, especially in children where the skull bone is thin and where little or no bone is left beneath the implant housing during surgery. An implant recess is first prepared using conventional surgical methods, and the implant housing is then pressed into the prepared recess to position the device in its final location. Housing fixation features in embodiments of the present invention resist sideways and downwards movement of the implant housing that may arise both during everyday use and case of high-energy external impacts. The implant housing is not fixed to the bone underneath the device, but rather to the surrounding bone around the opening of the implant recess; fixation is sideways into the bone and not from the top into the bone bed as in most other approaches. The fixation features can be either fixed or movable and can be located at various locations around the perimeter of the implant housing. At the same time, the implant device can be easily removed later if needed.

In contrast to engineering materials such as plastics or metals, living bone tissues will remodel over time to alleviate any significant static forces that might exist. One common example of such remodeling taking place is with the correction of teeth position using orthodontic braces— the static forces exerted by the braces (via the teeth) onto the bone displaces the teeth and over time remodels the bone. Similarly embodiments of the present invention described herein will cease to provide any significant static forces after some time once the skull bone has remodeled. Thus while initially at least one of the housing fixation features provides a spring force that helps fix the implant housing in the skull bone around the opening of the implant recess, eventually the implant housing will be sitting largely force-free in the bone.

Figure 1:
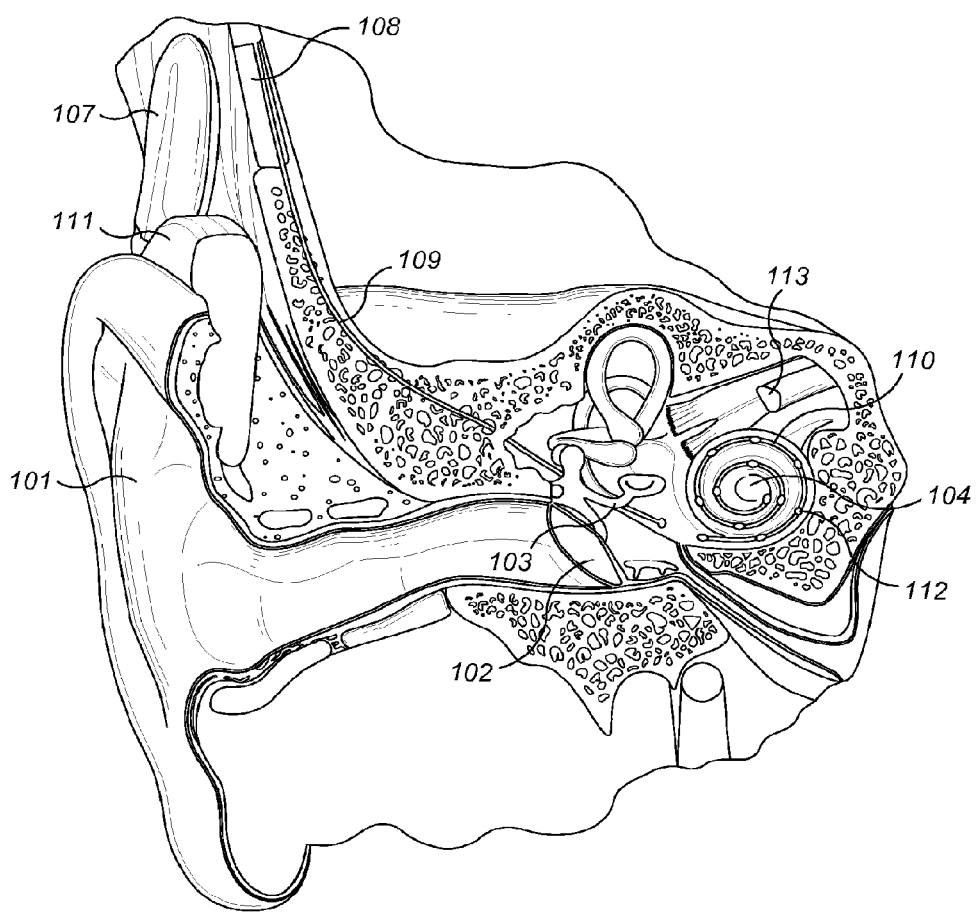
FIG. 1 shows various anatomical structures of the human ear and components of a typical cochlear implant system in relation thereto.
Figure 2A:
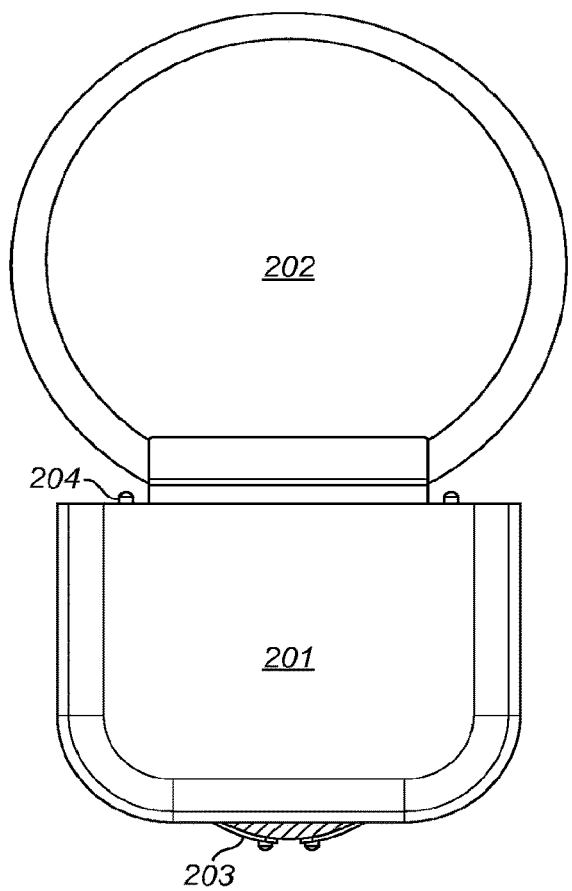
FIG. 2A-B shows a cochlear implant arrangement having housing fixation features according to an embodiment of the present invention.
Figure 2B:
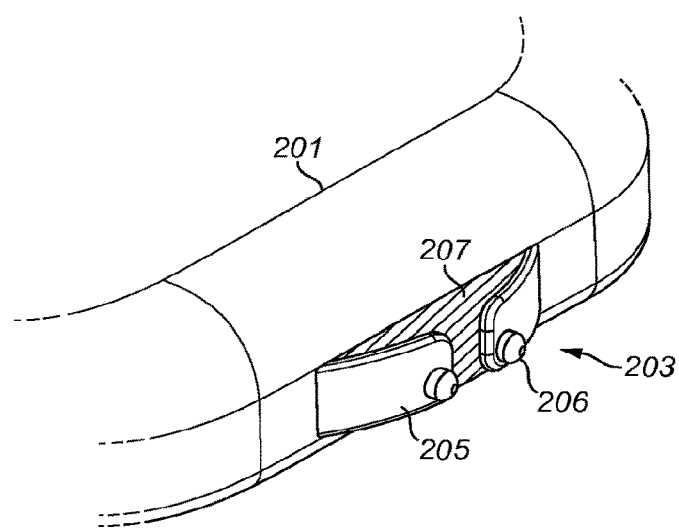

FIG. 2A-B shows a cochlear implant arrangement having housing fixation features according to one specific embodiment of the present invention. An implant receiver coil 202 receives communications signals from an external transmitter coil on the skin of the patient over the receiver coil. An implant housing 201 adjacent to the receiver coil 202 contains a stimulation processor for processing the communications signals to generate electrical stimulation signals for the cochlea of an implant patient. The implant housing 201 lies substantially in a flat plane and has an outer perimeter adapted to fit within a surgically prepared housing recess in skull bone of the implant patient.

Multiple housing fixation features 203 and 204 are located on the outer perimeter of the implant housing 201 and cooperate to develop lateral force in the plane of the implant housing 201 between the implant housing 201 and adjacent skull bone of the housing recess to fixedly secure the implant housing 201 within the housing recess.

The embodiment shown in FIGS. 2A-2B has multiple fixed contact pins 204 located toward one side of the outer perimeter of the implant housing 201. On the opposite side of the outer perimeter are a pair of elastic spring features 203. Here the spring features 203 are a pair of opposed cantilevered spring arms 205 anchored at opposite ends to the implant housing 201. The spring arms 205 are embedded in resiliently compressible material 207 such as silicone to avoid the regrowth of bone in between the spring arms 205 and the implant housing 201. If bone were to regrow in this gap it would be difficult or even impossible to push the spring arms 205 back without first removing the bone and device removal would be complicated. At the adjacent free ends of the spring arms 205 may be perpendicular to the spring pins 206.

The spring features 203 may be adapted to be bendable in a plane perpendicular to the plane of the implant housing 201. The spring features 203 generally are relatively small since they add area to the foot-print of the implant housing 201 and thus more bone needs to be removed before surgical placement of the device compared to a device without spring features. The relative position of the spring features 203 on the perimeter of the implant housing 201 is chosen to not be too near the upper surface of the implant housing 201 so that when the spring arms 205 expand they will extend into the adjacent bone with sufficient bone structure toward the outer surface of the skull bone to avoid splitting the bone. Typically the pins should have a distance of 1-2 mm from the outer surface of the skull bone to avoid such bone splitting which might arise following surgery due to the applied spring-forces or due to forces applied due to impact during wearing of the implant.

The housing fixation features 203 and 204 are made of biocompatible materials that are hard yet bendable, preferably metals such as titanium or hard polymers such as polyether ether ketone (PEEK). The specific dimensions and number of the housing fixation features 203 and 204 as well as their positions may be modified as needed for the specific design of the implant housing 201. In the embodiment shown in FIGS. 2A-2B, the elastic spring features 203 are free to bend only in the plane parallel to the implant housing 201. After the implant housing 201 has been implanted, the housing fixation features 203 and 204 become well-fixed to the bone and up and down movements of the implant housing 201 will be prevented.

Figure 3A:
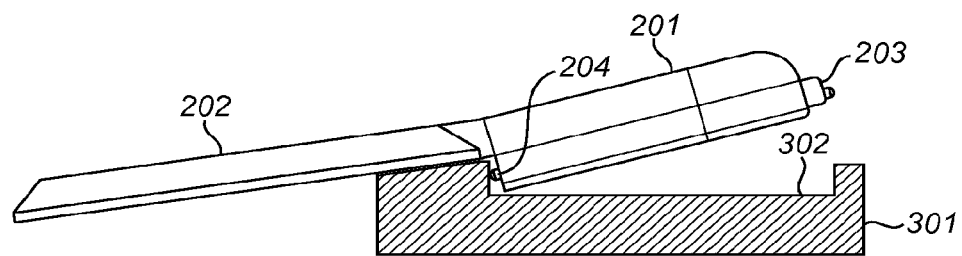
FIG. 3A-E shows aspects of an embodiment of a cochlear implant housing with regards to insertion into and removal from the housing recess in the skull bone.
Figure 3B:
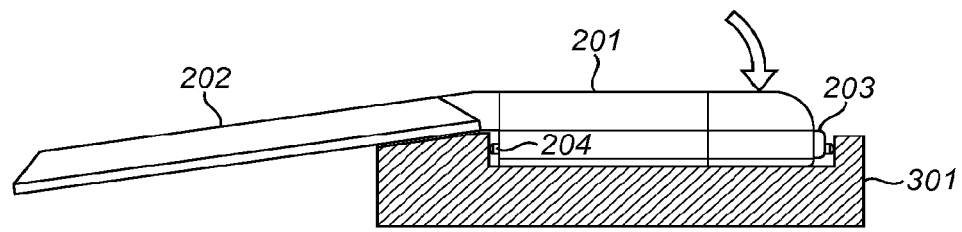

FIG. 3A-E shows insertion and removal of the implant 201 from the housing recess 302 in the skull bone 301. During implantation surgery it is common practice to cut through the skin and the periosteum at the future location of the implant housing 201 to allow precise drilling of the housing recess 302 in the skull bone 301. Subsequently a pocket is created under the periosteum (i.e. the periosteum is lifted off the skull bone 301 without cutting) next to the housing recess 302 where the receiver coil 202 will be placed. During implant placement the receiver coil 202 is first pushed sideways into the periosteal pocket coming to rest directly on the skull bone 301. In a next step the implant housing 201 is pushed into the housing recess 302. FIG. 3A shows in detail the initial surgical insertion maneuver where the coil-side of the implant housing 201 is first tipped at an angle to engage the skull bone 301 of the housing recess 302 with the fixed contact pins 204. The surgeon then rotates the implant housing 201 down into the housing recess 302 and by doing so automatically compresses the spring features 203 inward until the bottom of the implant housing 201 is flat against the skull bone 301 at the bottom of the housing recess 302, as shown in FIG. 3B. In the periosteal pocket the receiver coil 202 is limited in its movement perpendicularly to the skull bone 301 such that the rotational axis is best placed on the coil side of the implant housing 201. In other implant designs e.g. with the implant receiver coil placed within the implant housing 201, the rotational axis may be placed at other locations.

Figure 3C:
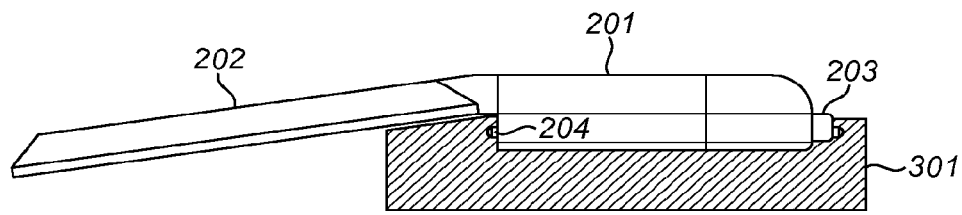
Figure 3D:
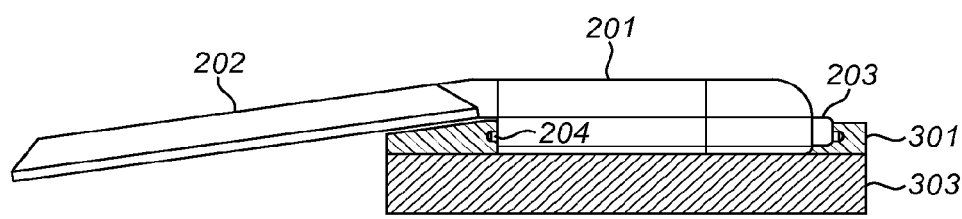

After surgical placement, the spring features 203 supply a sideways force to the skull bone 301 at the fixed contact pins 204 and thereby immediately fixes the implant housing 201 in the housing recess 302. Over time, growth of the skull bone 301 remodels inward around the fixed contact pins 204 and the spring features 203 to alleviate the force from the spring features 203 and fixedly secure the implant housing 201 in the housing recess 302, as shown in FIG. 3C. FIG. 3D shows the final condition for patients with thin skull bone 301 (typically children) where there is little or no skull bone 301 directly beneath the implant housing 201 which lies against the dura mater of the brain 303.

Figure 3E:
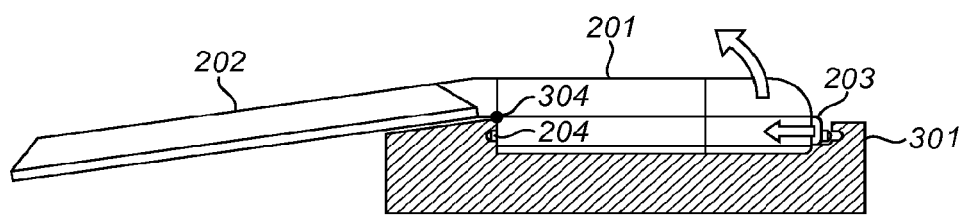
Figure 4A:
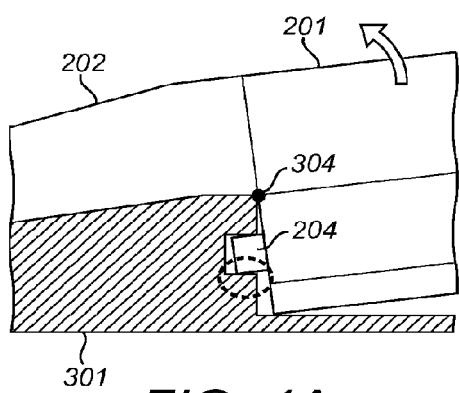
FIG. 4A-H shows details of the fixed contact pins in various embodiments.
Figure 4B:
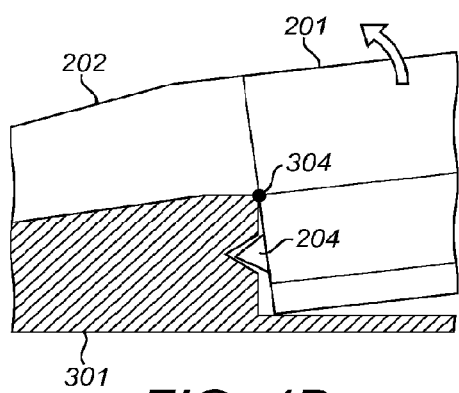
Figure 4C:
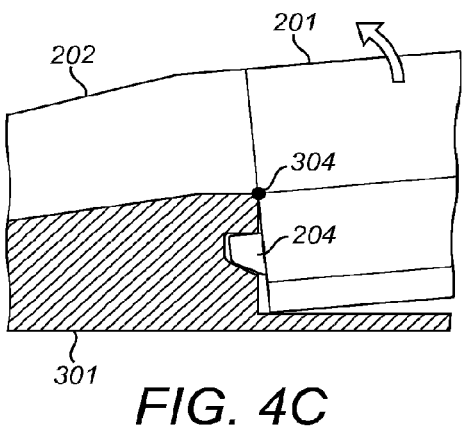
Figure 4D:
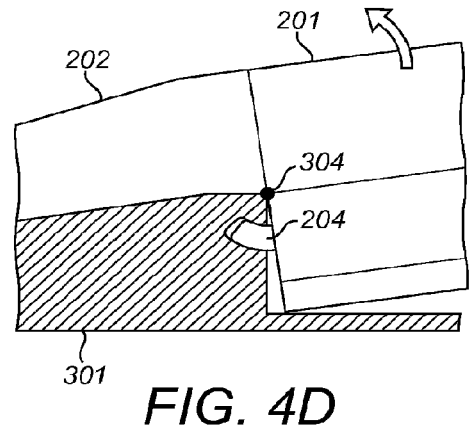

To later remove the implant housing 201, the surgeon compresses the spring features 203 back against the implant housing 201 to remove the spring pins 206 from the skull bone 301, and rotates the device about an axis 304 on the opposite side as can be seen in FIG. 3E to remove the fixed contact pins 204 from the skull bone 301. It is important that the geometry of the fixed contact pins 204 accommodates such device removal procedures since the pins eventually will be tightly surrounded by bone tissue. As seen in FIG. 4A, when the fixed contact pins 204 have a long straight non-tapered shape, it is not easy to rotate the implant housing 201 about the axis 304 without either breaking the adjacent skull bone 301 or deforming the fixed contact pins 204. FIG. 4B shows a conical shaped fixed contact pin 204, FIG. 4C shows a tapered shape fixed contact pin 204, and FIG. 4D shows a curved shape fixed contact pin 204, all of which are more easily compatible with rotating the implant housing 201 about the axis 304 for removing the device without damaging the skull bone 301.

Figure 4E:
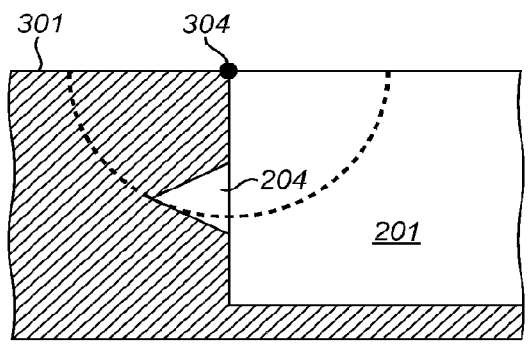
Figure 4F:
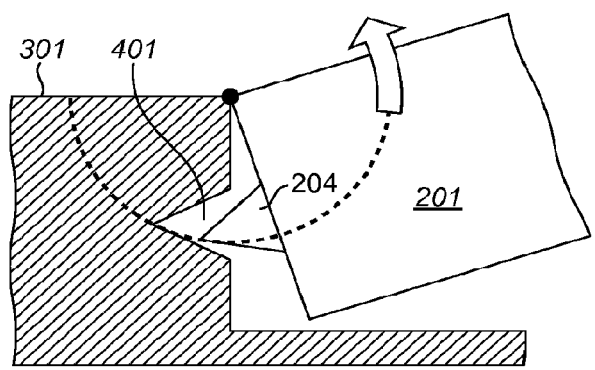
Figure 4G:
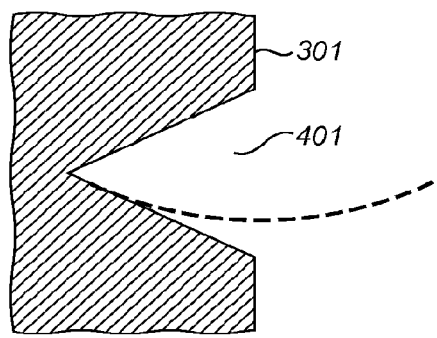
Figure 4H:
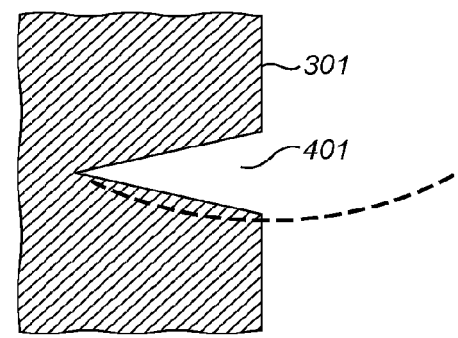

FIG. 4E-G show in detail an example of how the pin geometry of FIG. 4B allows unproblematic removal. During device removal, as shown in FIGS. 4E and 4F, the tip of the triangular contact pin 204 will be rotated at out the pin recess 401 in a counter-clockwise direction along a circular path (broken line with it center around the axis 304) with this line not passing through skull bone 301 (see enlarged view in FIG. 4G where the broken line does not reach into the patterned area of the skull bone 301). For a contact pin 204 of similar but thinner shape (FIG. 4H) the path of the pin tip would go through the skull bone 301 and thus would represent a problematic device removal situation.

Figure 5A:
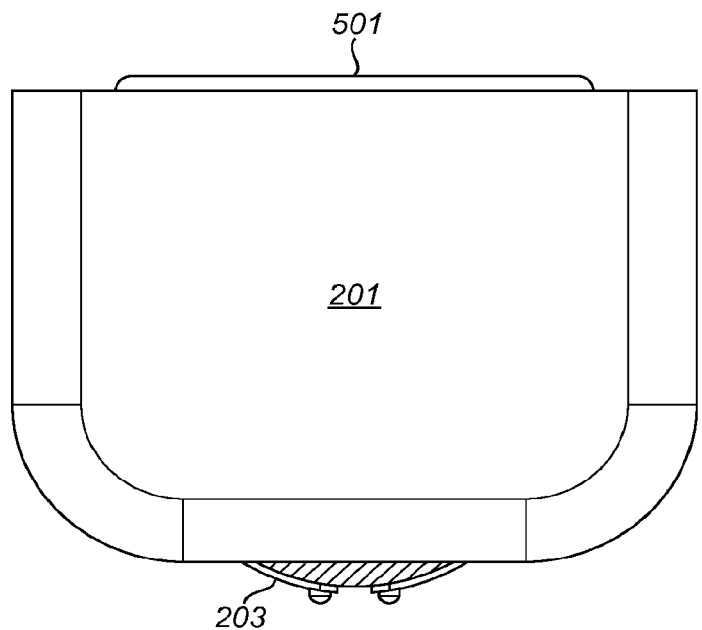
FIG. 5A-B shows an embodiment of a cochlear implant housing having a fixed contact strip.
Figure 5B:
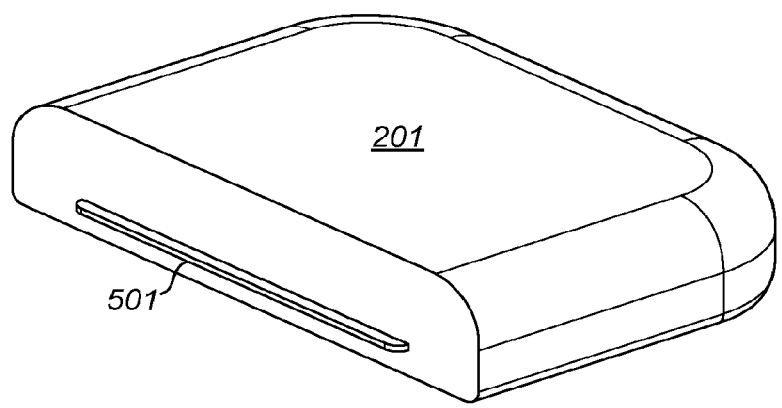

FIG. 5A-B shows an embodiment of a cochlear implant housing having an elongated contact strip 501 along a portion of the outer perimeter of the implant housing 201 rather than multiple fixed contact pins. This contact strip 501 has the same function as the fixed contact pins 204 in the previous embodiment. The dimensions of the contact strip 501 may be modified as needed and/or multiple contact strips 501 may be used as alternative to only one strip. The contact strip 501 should have an appropriate geometry as discussed above with regards to FIGS. 4A-D to allow rotation of the implant housing 201 out of the skull bone 301.

Figure 6A:
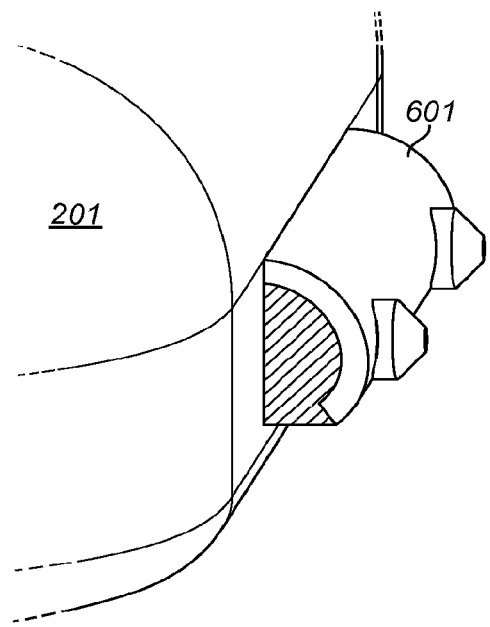
FIG. 6A-B show details of alternative elastic spring features according to embodiments of the present invention.
Figure 6B:
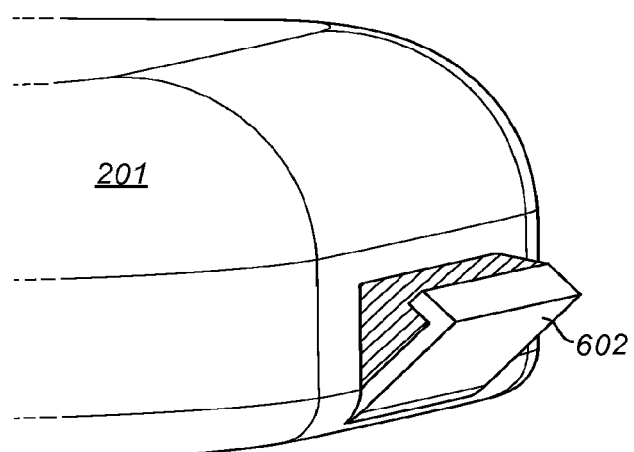

FIG. 6A shows an embodiment of the invention that uses a spring feature 601 that is only free to bend in a plane perpendicular to the plane of the implant housing 201. An elastic and biocompatible resiliently compressible material such as silicone may be used to avoid regrowth of bone in between the spring feature 601 and the implant housing 201. FIG. 6B shows another embodiment having a spring feature 602 without pins. The sharp bend of the spring feature 602 will over time move into the bone to provide secure fixation.

Figure 7A:
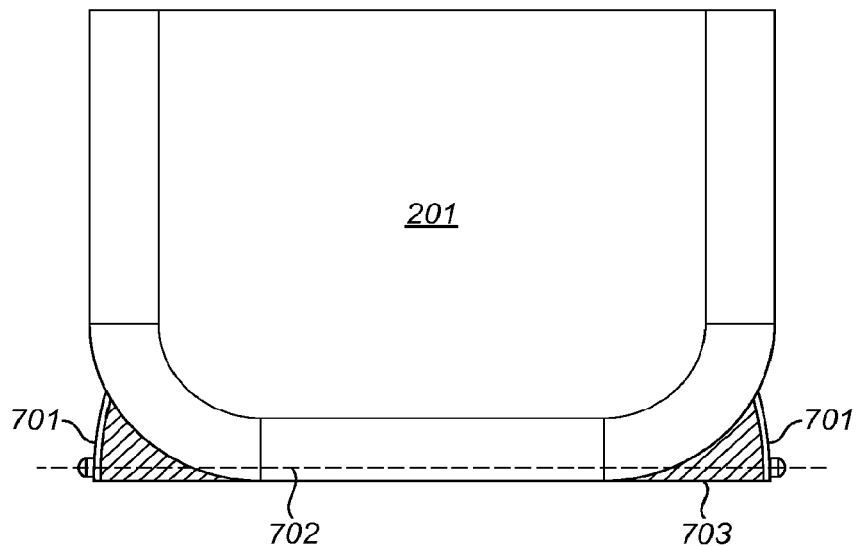
FIG. 7A-B show details of an alternative elastic spring feature according to an embodiment of the present invention.
Figure 7B:
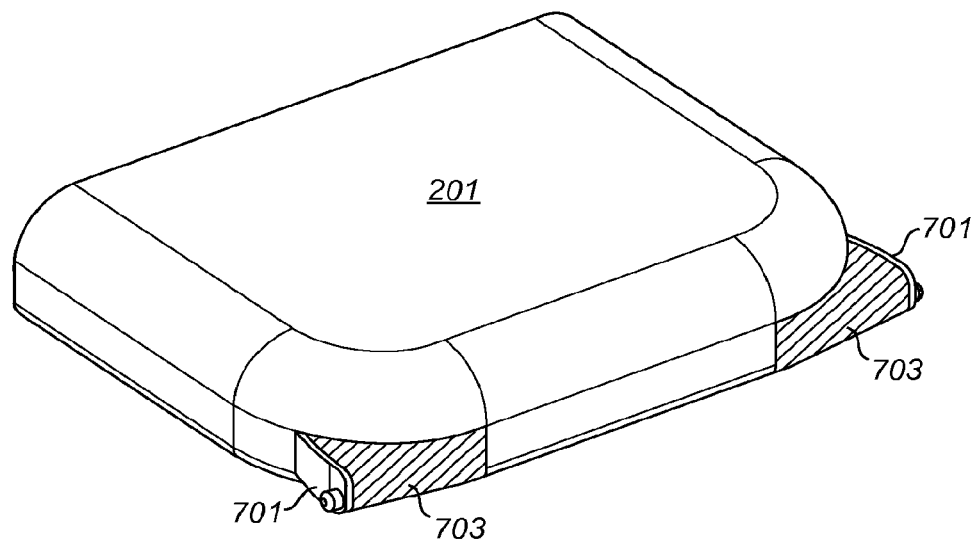

Some embodiments may not necessarily have any fixed contact features provided an appropriate spring feature structure is implemented. For example, FIG. 7A-B show details of an embodiment having two spring pins 701 located on opposite sides of the implant housing 201 that are compressible in towards each other along a pin axis 702 tangent to the outer perimeter of the implant housing 201. The geometry shown would permit some rotation of the implant housing 201 around the of the pin axis 702 thus there may not be quite as good a fixation of the device as in many of the previously described embodiments.

Figure 8A:
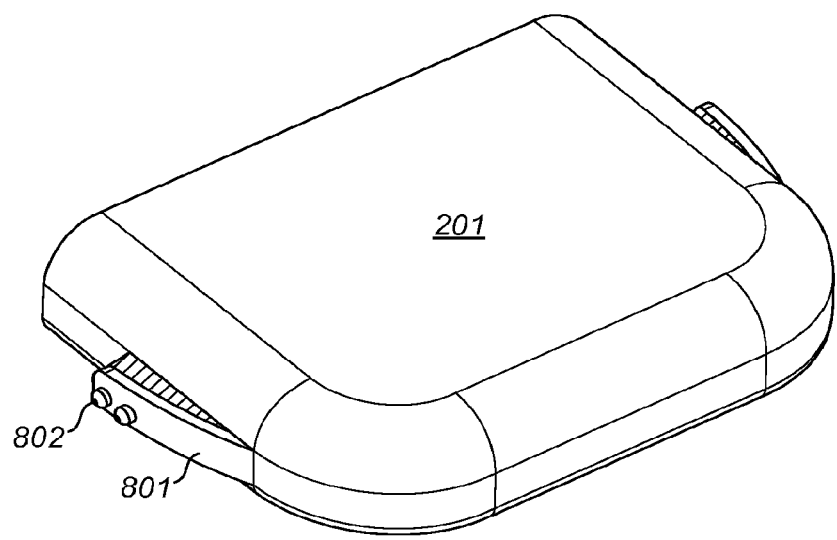
FIG. 8A-B show details of alternative elastic spring features according to embodiments of the present invention.
Figure 8B:
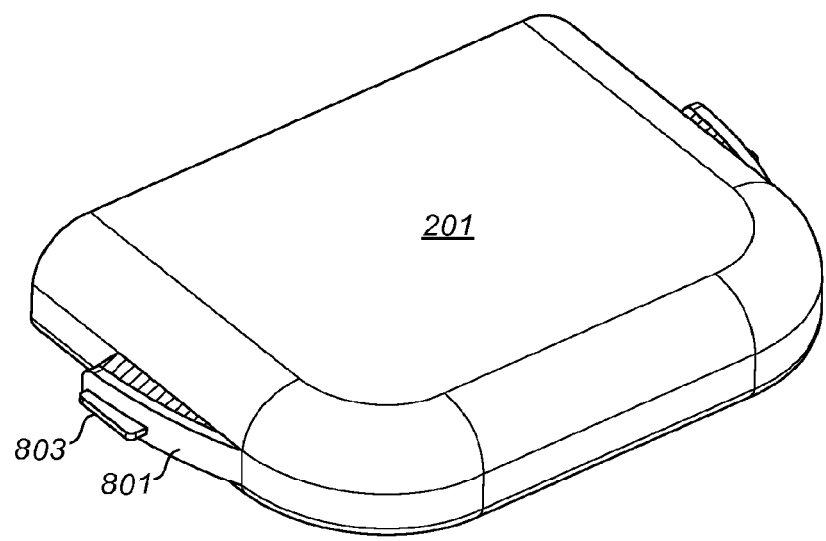

FIG. 8A-B show details of an alternative elastic spring feature arrangement similar to that in FIG. 7A-B where the two spring arms 801 are moved further towards the coil side of the implant housing 201 so as to lie along a chord across the outer perimeter. In the embodiment shown in FIG. 8A, there are multiple spring pins 802 on the spring arms 801 which act as rotation resisting features adapted to resist rotation of the implant housing 201 within the housing recess. FIG. 8B shows spring arms 801 having a contact strip 803 that both engages the skull bone in the implant opening and resists rotation of the implant housing 201.

Besides a structural mechanical spring element as described above, some embodiments of the present invention may be based on one or more polymer material spring elements. That is spring features can be formed from relatively hard silicone material that when compressed direct forces onto the surrounding skull bone of the implant opening and can thereby over time drive fixed pins into the bone. The relatively hard silicone material of the polymer springs is different from the relatively softer and more resilient silicone material described previously which is used to avoid bone re-growth between the spring features and the implant housing.

In such embodiments, a polymer spring element alone may not by itself be sufficient to effectively fixate the implant housing, and so some additional more rigid structures may also be needed. The polymer spring element may be used just for sideways pressing force (e.g. fixed metal pins on the opposite side of the implant housing) into the skull bone without providing fixation to the bone. Alternatively or in addition, rigid structures (again, for example, metal pins) may also be placed on or in the polymer spring element so as to additionally fixate the implant housing to some extent. It is best to have multiple fixation points around the perimeter of the implant housing to provide the best possible device immobilization.

Figure 9A:
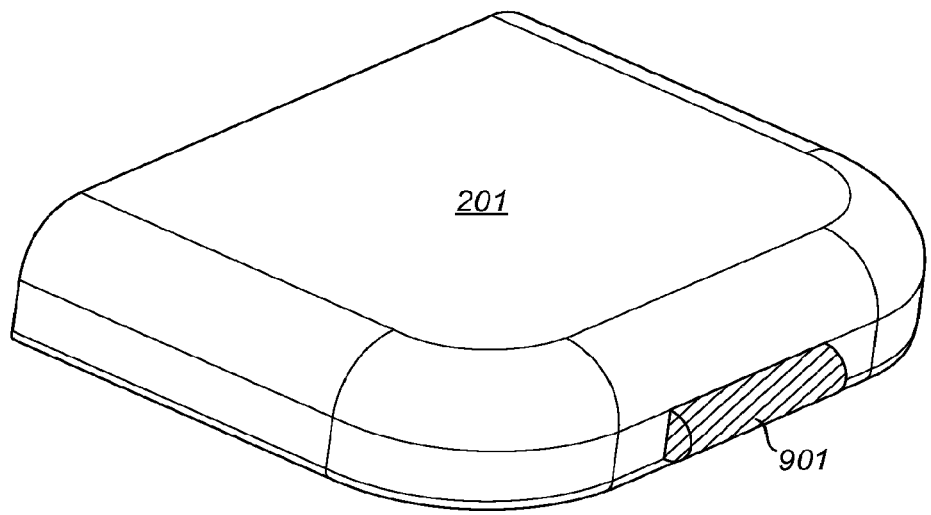
FIG. 9A-B show details of alternative polymer spring features according to embodiments of the present invention.
Figure 9B:
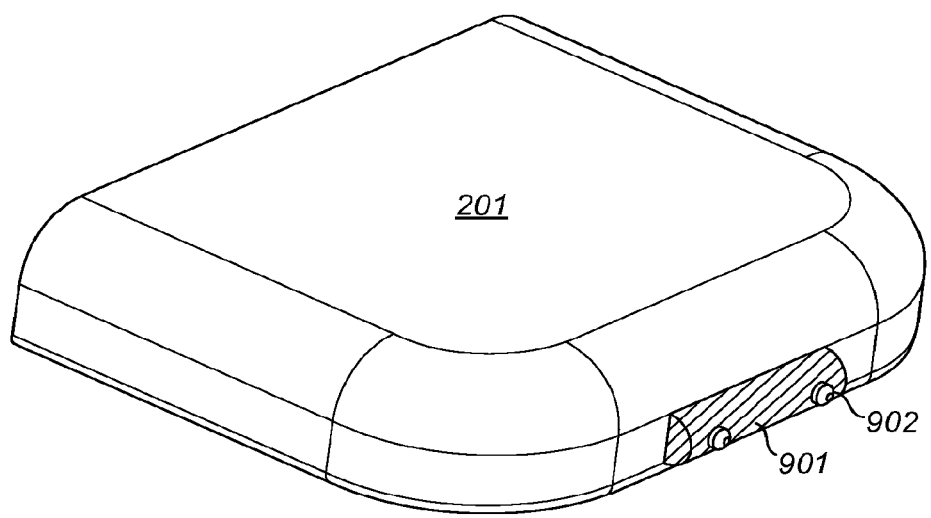

FIG. 9A shows details of one such embodiment where there are one or more fixation features (not shown) on one side of the implant housing 201, and a polymer spring element 901 on the opposite side. The polymer spring element 901 provides a sideways force that over time pushes the fixation features into the bone. But the polymer spring element 901 does not itself provide good fixation at its own position. FIG. 9B shows a similar polymer spring element 901 to which is added two embedded spring pins 902 pins to provide improved fixation on that side of the implant housing 201. Due to the multi-directional flexibility of the polymer spring element 901, the exerted force may press the implant housing 201 in more than one direction tending to correct any misfit between the implant housing 201 and the housing recess. The location of the spring element 901 on the perimeter of the implant housing 201 enables visible confirmation of engagement between the spring element 901 and the adjacent bone around housing recess when the implant housing 201 is properly positioned in the housing recess.

Figure 10A:
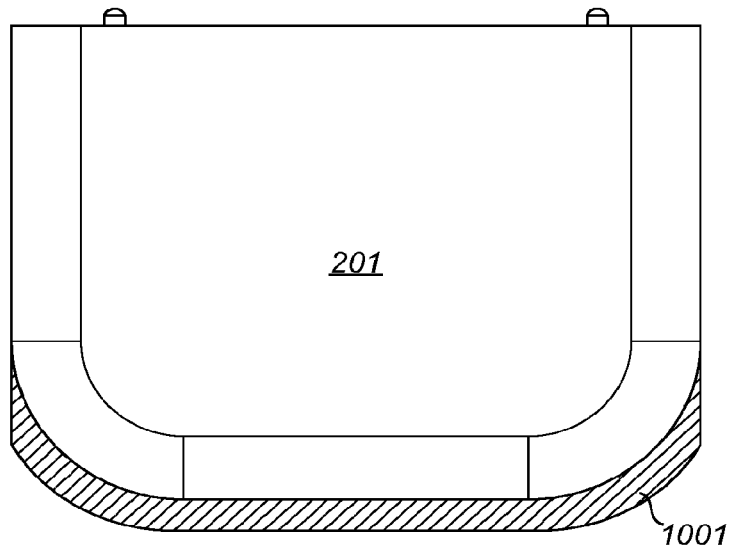
FIG. 10A-B show details of an alternative polymer spring feature according to an embodiment of the present invention.
Figure 10B:
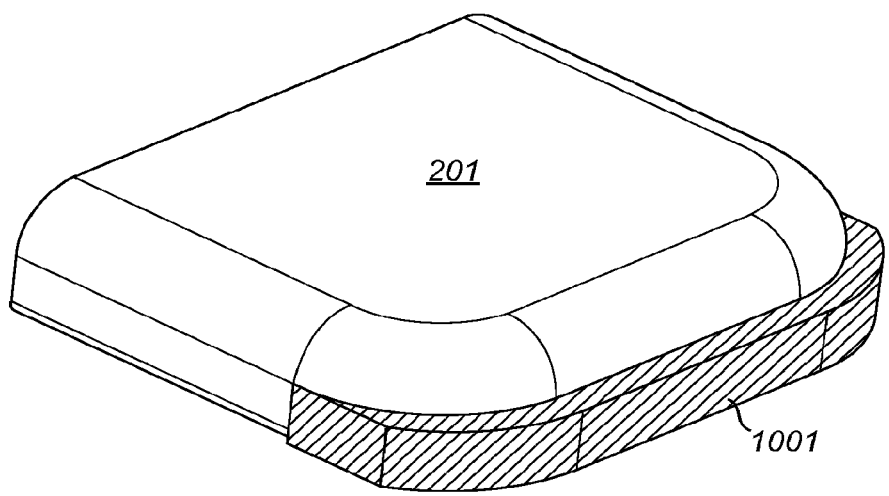

FIG. 10A-B show details of an alternative polymer spring feature according to an embodiment of the present invention. Here the polymer spring element 1001 covers one whole side of the implant housing 201 and wraps around the ends. In contrast to some of the previous embodiments, an embodiment of an implant housing 201 with a polymer spring element 1001 that extends around the ends of one side does not necessarily require rotationally adapted fixation features. The spring element 1001 may have a trapezoid cross-section to avoid an upward force, if, for example, the lateral wall of the housing recess lacks an exact perpendicular direction in relation to the skull bone. When the elastic spring element 1001 is deformed, the trapezoid shape ensures that the elastic forces do not contain a force component into the upward direction that might push the implant housing 201 out from the housing recess. Alternatively, the spring element 1001 may have an asymmetric triangular cross-section which exerts the desired elastic forces without any upward component.

Figure 11A:
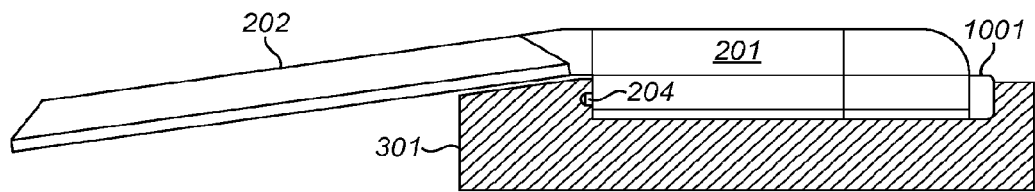
FIG. 11A-B shows aspects of an embodiment of a cochlear implant housing with regards to insertion into and removal from the housing recess in the skull bone.
Figure 11B:
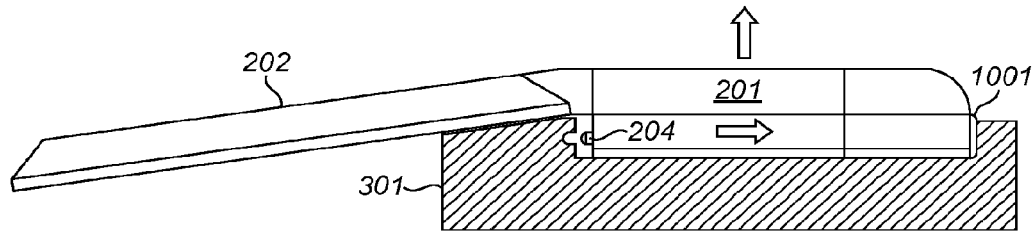

As shown in FIG. 11A-B, the implant housing 201 can be removed from the skull bone 301 without rotational movement, simply by pressing the implant housing 201 directly away from fixation features 204 and then lifting up. By pushing the implant housing 201 towards the polymer spring element 1001, the fixation features 204 are retracted from the skull bone 301 allowing device removal. Note that such pushing is only possible when the polymer spring element 1001 covers one whole side of the implant housing 201, and that the height of the polymer spring element 1001 needs to be at least equivalent to the depth to which the implant housing 201 is recessed into the skull bone 301. Furthermore, to allow full extraction of the fixation features 204 from the skull bone 301 before lifting up the implant housing 201, the length of the fixation features 204 will need to be less than the compressible distance of the polymer spring element 1001. This type of design increases the footprint area of the implant housing 201 to a greater extent than previous embodiments.

Figure 12A:
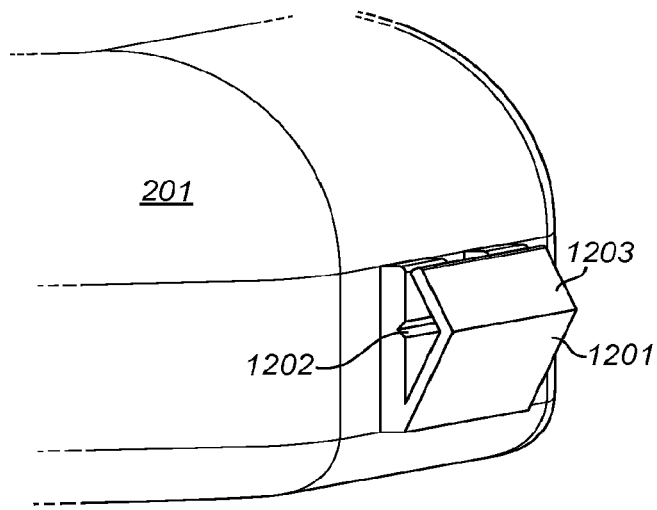
FIG. 12A-B show details of an alternative active fixation feature according to an embodiment of the present invention.
Figure 12B:
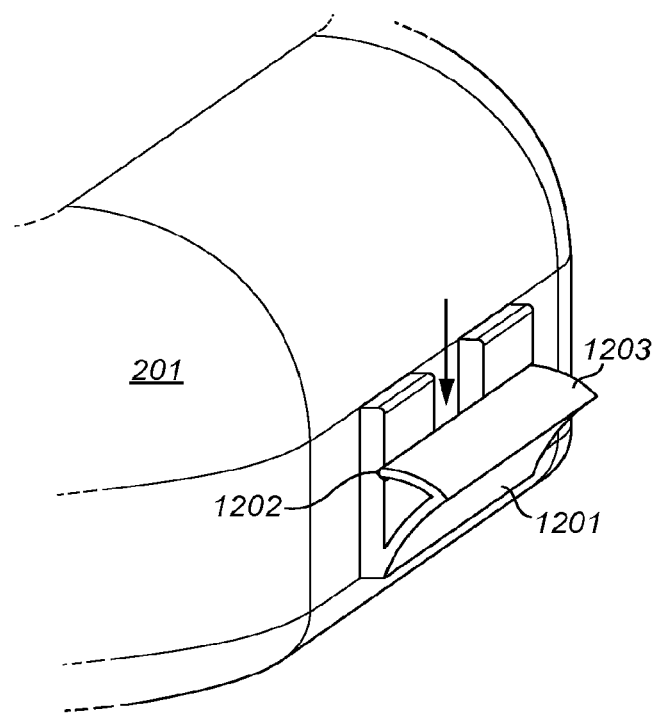

An alternative to passive spring features as described above is what can be characterized as active fixation features. FIG. 12A-B show details of an alternative embodiment having such an active fixation feature. Initially, as shown in FIG. 12A, the implant housing 201 with an extendable arm feature 1201 is placed by the surgeon into an implant opening in the skull bone of appropriate size and shape. The extendable arm feature 1201 can be moved away from the implant housing 201 by using a surgical tool to press down on the top edge 1203 of the extendable arm feature 1201 that the middle fold of the extendable arm feature 1201 moves out away from the implant housing 201 until the top edge 1203 of the extendable arm feature 1201 fits into a locking groove 1202. The extended middle edge of the extendable arm feature 1201 presses against the adjacent skull bone at the implant opening with sideways pressure to securely fix the implant housing 201 in place. The extendable arm feature 1201 is embedded in resiliently compressible material such as silicone to avoid regrowth of bone in-between the arm feature 1201 and the implant housing 201.

One difference from the previously described embodiments is that this type of active fixation mechanism is not effective until the surgeon specifically activates it. In the earlier embodiments, fixation of the implant housing was achieved as soon as it was pressed into the implant opening in the skull bone since the spring features were compressed by the placement motion. Thus the implant housing was fixed without needing any further actions. But with embodiments using one or more active fixation features, it is not enough to just place the implant housing into the implant opening in the skull bone. Some surgical activating motion is required.

In some embodiments, the fixation force could be adjustable, for example, by turning a screw mechanism some variable number of rotations. In other embodiments, an activated feature could act as an on/off switch to move the extendable arm either fully out or fully, like turning a key to lock or unlock a door.

Figure 13:
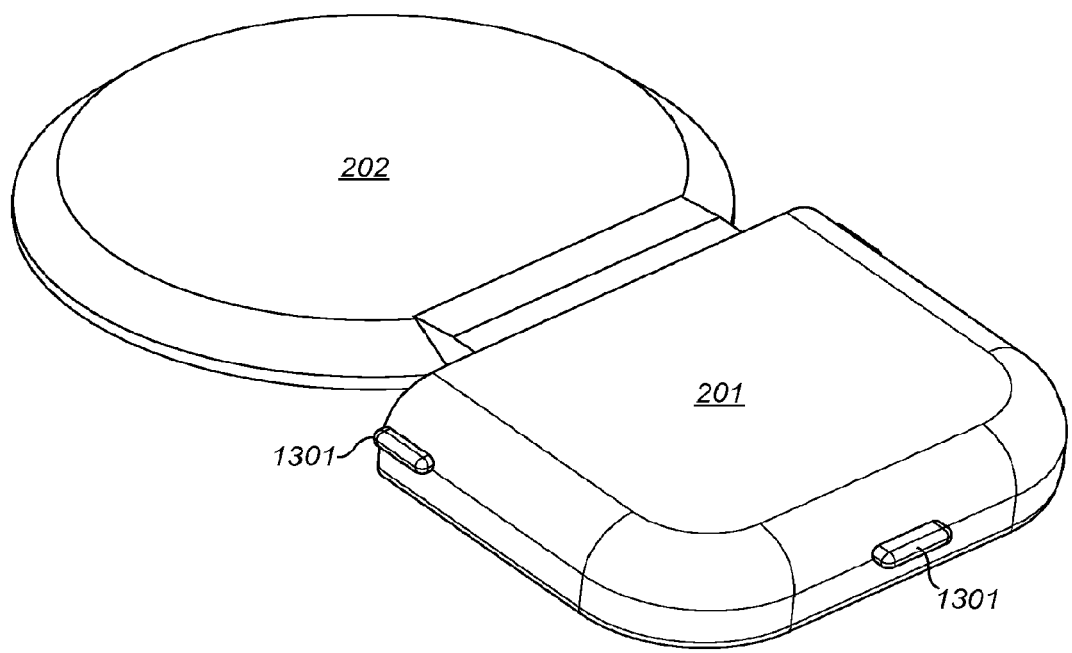
FIG. 13 shows an example of a cochlear implant housing having implant protection features according to an embodiment of the present invention.

Some embodiments may further include multiple implant protection features that are located on the outer perimeter of the implant housing and that protrude above the outer surface of the skull bone around the housing recess to resist inward displacement of the implant housing in response to an external impact force normal to the implant housing. FIG. 13 shows one example of a cochlear implant housing 201 having such multiple implant protection features 1301. The housing recess in the skull bone is prepared using conventional methods, and the implant housing 201 is then placed in the housing recess to place it in its final position. The fixed impact protection features 1301 standing out from the side of the implant housing 201 above the bone level at the opening of the housing recess then come to rest on the adjacent bone surface. In case of an external impact onto the implant housing 201, the impact protection features 1201 resting on the skull bone transfer the impact energy to the bone around the implant housing 201, thereby preventing the implant housing 201 from moving in towards the brain (which, to be clear, would be bad).

In this embodiment, there is one impact protection feature 1301 on each side of the implant housing 201 that does not attach to the receiver coil 202. The side facing towards the implant coil 202 is prevented from downwards displacement by the attachment to the receiver coil 202 which is located on top of the skull bone, and by the two impact protection features 1301 closest to the receiver coil 202. The impact protection features 1301 are placed at approximately at the half height/thickness of the implant housing 201, allowing it to be recessed about halfway into the skull bone before the impact protection features 1301 contact the bone and prevent further downward movement.

When used in combination with the above described embodiments having fixation features, the impact protection features also serves to limit the depth to which the implant housing is recessed when it is being pressed into the housing recess. This prevents that the implant housing is pressed too deeply into the housing recess which could necessitate removal and renewed placement. For maximum stability during an impact, the impact protection features should not be located directly at the same radial position on the perimeter of the implant housing because the skull bone in these areas is thinner than at other locations (a certain bone volume is taken up by the fixation features), and therefore less impact energy would be tolerated before fracturing. The number, size and location of the impact protection features may however be varied to allow maximum protection for the specific housing design.

Fixation arrangements such as those described above are easy to use, and allow easy device removal. Passive spring fixation systems only need to be positioned into the housing recess, whereas active fixations systems require a bit more effort and in general may be more complicated in design (especially if there are small screws and threads etc.).

All the described embodiments attach to the skull bone found around the implant housing (rather than the bone beneath the housing) thus allowing reliable fixation even in thin skull bones. And since the systems are built into the devices, the implanting surgeons are forced to use them and this helps to assure an overall consistent fixation quality of the implants. The implant housing may have one or more grasping recesses that allow a surgical tool to be inserted for help during explantation of the device. The grasping recesses may be located on the housing to enable easy rotation of the housing about a rotational axis which may be parallel to fixation pins. Then when the implant housing is rotated within the housing recess, the fixation pin is pushed out from the recess that may exist when the spring element expands.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant arrangement comprising:
an implant housing containing a stimulation processor for processing externally produced communications signals to generate electrical stimulation signals for the cochlea of an implant patient, the implant housing lying substantially in a plane and having an outer perimeter adapted to fit within a surgically prepared housing recess in skull bone of the implant patient; and
a plurality of housing fixation features located on the outer perimeter, the housing fixation features being adapted to cooperate to develop lateral force in the plane of the implant housing between the implant housing and radially adjacent skull bone of the housing recess to fixedly secure the implant housing within the housing recess,
wherein the housing fixation features include one or more fixed contact features located toward one side of the outer perimeter and one or more elastic spring features located towards another side of the outer perimeter.

2. The arrangement according to claim 1, wherein the outer perimeter further comprises a resiliently compressible material and wherein the spring features are embedded in the resiliently compressible material.

3. The arrangement according to claim 1, wherein the spring features are adapted to be bendable in a plane perpendicular to the housing plane.

4. The arrangement according to claim 1, wherein the spring features include an elongated contact strip along a portion of the outer perimeter.

5. The arrangement according to claim 1, wherein the spring features include a pair of elastic spring pins.

6. The arrangement according to claim 5, wherein the spring pins are compressible in towards each other along an axis tangent to the outer perimeter.

7. The arrangement according to claim 5, wherein the spring pins are compressible in towards each other along a chord across the outer perimeter.

8. The arrangement according to claim 5, wherein the spring pins include one or more rotation resisting features adapted to resist rotation of the implant housing within the housing recess.

9. The arrangement according to claim 1, wherein the spring features are formed of metal spring material.

10. The arrangement according to claim 1, wherein the spring features are formed of elastic polymer material.

11. The arrangement according to claim 1, wherein the fixed contact features include an elongated contact strip along a portion of the outer perimeter.

12. The arrangement according to claim 1, wherein the fixed contact features include a plurality of fixed contact pins.

13. The arrangement according to claim 1, wherein the fixed contact features are shaped to allow an opposite side of the outer perimeter to be lifted up out of the housing recess without damaging the skull bone around the fixed contact features.

14. The arrangement according to claim 1, wherein the housing fixation features include active features adapted to be manually operated during insertion surgery to fixedly secure the implant housing within the housing recess.

15. The arrangement according to claim 14, wherein the active features are based on a screw mechanism.

16. The arrangement according to claim 1 further comprising:
a receiver coil adjacent to the implant housing for receiving the communications signals from an external transmitter coil on the skin of the patient over the receiver coil.

17. The arrangement according to claim 1, wherein the implant housing further comprises:
a plurality of implant protection features located on the outer perimeter and adapted to protrude above the outer surface of the skull bone around the housing recess to resist inward displacement of the implant housing in response to an external impact force normal to the implant housing.

* * * * *